United States Patent
Reardon et al.

(10) Patent No.: US 12,271,057 B1
(45) Date of Patent: Apr. 8, 2025

(54) CHROMATIC ABERRATION TUNING OPHTHALMIC CORRECTOR LENS METHODS

(71) Applicants: The UAB Research Foundation, Birmingham, AL (US); Board of Trustees of the University of Albama, for and behalf of the University of Albama in Huntsville, Huntsville, AL (US)

(72) Inventors: Patrick John Reardon, Madison, AL (US); Timothy Jerner Gawne, Birmingham, AL (US); Thomas Tolles Norton, Homewood, AL (US)

(73) Assignees: The UAB Research Foundation, Birmingham, AL (US); Board of Trustees of the University of Albama, for and behalf of the University of Alabama Huntsville, Huntsville, AL (US)

( * ) Notice: Subject to any disclaimer, the term of this patent is extended or adjusted under 35 U.S.C. 154(b) by 589 days.

(21) Appl. No.: 17/129,727

(22) Filed: Dec. 21, 2020

Related U.S. Application Data

(60) Provisional application No. 62/951,869, filed on Dec. 20, 2019.

(51) Int. Cl.
*A61B 3/028* (2006.01)
*A61B 3/00* (2006.01)
*G02C 7/02* (2006.01)

(52) U.S. Cl.
CPC ............ *G02C 7/027* (2013.01); *A61B 3/0008* (2013.01); *A61B 3/0025* (2013.01); *A61B 3/028* (2013.01);
(Continued)

(58) Field of Classification Search
CPC . G02C 7/04; G02C 7/06; G02C 7/022; G02C 7/024; G02C 7/027; G02C 7/041;
(Continued)

(56) References Cited

U.S. PATENT DOCUMENTS

| 4,641,934 | A | * | 2/1987 | Freeman | .................. A61F 2/14 623/6.31 |
| 5,671,754 | A | | 4/1997 | Hoffman | |

(Continued)

FOREIGN PATENT DOCUMENTS

| AU | 2015256283 B2 | 5/2020 | |
| CN | 101394809 A * | 3/2009 | ............. A61F 9/008 |

(Continued)

OTHER PUBLICATIONS

Jochen Straub, Design, Validation and Application of an Ocular Shack-Hartmann Aberrometer, 2003, pp. 1-253 [online], [retrieved Apr. 26, 2023], retrieved from the Internet <URL: https://repository.arizona.edu/bitstream/handle/10150/289957/azu_td_3107043_sip1_m.pdf?sequence=1 >. (Year: 2003).*

(Continued)

*Primary Examiner* — Cara E Rakowski
*Assistant Examiner* — Wesley Scott Ashton
(74) *Attorney, Agent, or Firm* — Butler Snow LLP; Jon E. Holland

(57) ABSTRACT

The present disclosure is directed to methods of tuning chromatic aberration of the eyes of a subject for the treatment of myopia. Refractive errors of an eye of the subject are assessed in the presence of one or more of red, blue, or green colored light, individually. A hybrid achromatic lens having a refractive portion and a diffractive portion is then designed, with the hybrid lens having a distribution of power varied between the refractive portion and diffractive portion. As such, the hybrid lens produces a state of chromatic (Continued)

aberration for the eyes of the subject capable of reducing or eliminating myopia advancement for the eyes of the subject.

10 Claims, 14 Drawing Sheets

(52) U.S. Cl.
CPC ..... *G02C 2202/10* (2013.01); *G02C 2202/20* (2013.01); *G02C 2202/22* (2013.01); *G02C 2202/24* (2013.01)

(58) Field of Classification Search
CPC ........ G02C 7/042; G02C 7/044; G02C 7/081; G02C 7/107; G02C 7/108; G02C 2202/10; G02C 2202/20; G02C 2202/22; G02C 2202/24; A61B 3/0008; A61B 3/0025; A61B 3/028
See application file for complete search history.

(56) References Cited

U.S. PATENT DOCUMENTS

| | | | |
|---|---|---|---|
| 6,000,798 A | 12/1999 | Chipman et al. | |
| 6,183,084 B1* | 2/2001 | Chipman | G02C 7/068 351/159.52 |
| 6,830,332 B2* | 12/2004 | Piers | G02B 5/1895 623/6.31 |
| 7,677,725 B2* | 3/2010 | Piers | G02B 5/1814 623/6.31 |
| 7,971,996 B2 | 7/2011 | Drobe et al. | |
| 8,192,022 B2* | 6/2012 | Zalevsky | A61F 2/1613 351/159.73 |
| 8,709,079 B2* | 4/2014 | Zhang | G02C 7/041 623/6.31 |
| 9,182,228 B2 | 11/2015 | Pollack et al. | |
| 9,541,773 B2* | 1/2017 | Bakaraju | A61F 2/1637 |
| 9,733,494 B2* | 8/2017 | Brennan | A61F 2/16 |
| 10,061,143 B2* | 8/2018 | Brennan | G02C 7/041 |
| 10,624,735 B2* | 4/2020 | Canovas Vidal | G02B 27/0075 |
| 11,061,255 B2* | 7/2021 | Lau | G02C 7/086 |
| 11,567,347 B2* | 1/2023 | Sankaridurg | G02C 7/041 |
| 2004/0179167 A1* | 9/2004 | Dahi | B29D 11/0048 351/159.68 |
| 2004/0212779 A1* | 10/2004 | Dahi | G02C 7/04 351/159.14 |
| 2006/0232743 A1* | 10/2006 | Legerton | G02C 7/02 623/6.11 |
| 2008/0151183 A1* | 6/2008 | Altmann | G02C 7/041 351/159.6 |
| 2008/0218687 A1 | 9/2008 | Phillips | |
| 2009/0141235 A1 | 6/2009 | Collins et al. | |
| 2010/0036489 A1 | 2/2010 | Lindacher et al. | |
| 2012/0062836 A1 | 3/2012 | Tse et al. | |
| 2012/0194780 A1 | 8/2012 | Back | |
| 2012/0206691 A1 | 8/2012 | Iwai | |
| 2015/0085247 A1 | 3/2015 | Brien et al. | |
| 2016/0334643 A1* | 11/2016 | Hyde | G02C 7/04 |
| 2017/0115509 A1* | 4/2017 | Brennan | G02C 7/044 |
| 2017/0276959 A1 | 9/2017 | Bowers | |
| 2017/0276961 A1 | 9/2017 | Wooley et al. | |
| 2017/0276963 A1* | 9/2017 | Brennan | G02C 7/081 |
| 2018/0095296 A1 | 4/2018 | Lin et al. | |
| 2018/0228364 A1 | 8/2018 | Brennan et al. | |
| 2018/0373059 A1 | 12/2018 | Lin et al. | |
| 2019/0302322 A1 | 10/2019 | Chung et al. | |
| 2020/0073147 A1* | 3/2020 | Bakaraju | G02C 7/022 |
| 2021/0191153 A1* | 6/2021 | Borja | G02C 7/042 |
| 2021/0191154 A1* | 6/2021 | Borja | G02C 7/042 |
| 2022/0342233 A1 | 10/2022 | Gawne et al. | |

FOREIGN PATENT DOCUMENTS

| | | | | |
|---|---|---|---|---|
| CN | 109975995 A | | 7/2019 | |
| EP | 2781899 A2 | | 9/2014 | |
| KR | 1020140074271 A | | 6/2014 | |
| TW | 1500993 B | | 9/2015 | |
| WO | WO-2012034265 A1 * | | 3/2012 | ............... A61F 2/14 |
| WO | 2012173891 A1 | | 12/2012 | |
| WO | 2013015743 A1 | | 1/2013 | |
| WO | 2018076057 A1 | | 5/2018 | |
| WO | 2018106657 A1 | | 6/2018 | |
| WO | WO-2018152596 A1 * | | 8/2018 | ......... G02B 27/0075 |
| WO | WO-2018195600 A1 * | | 11/2018 | ............. A61F 2/145 |
| WO | 2021055162 A1 | | 3/2021 | |

OTHER PUBLICATIONS

S. Marcos, Aberrometry: Basic Science and Clinical Applications, 302 Bull. Soc. Belge Ophtalmol. 197-213 (2006). (Year: 2006).*
Cathleen Fedtke et al., The BHVI-EyeMapper: Peripheral Refraction and Aberration Profiles, 91 Optometry and Vision Science 1199-1207 (2014). (Year: 2014).*
Visible Light Spectrum From a Lighting Manufacturer's Perspective, 2018, pp. 1-14 [online], [retrieved Mar. 23, 2023], retrieved from the Internet <URL: https://www.lumitex.com/hubfs/docs/visible-light-spectrum-1.pdf>. (Year: 2018).*
Other Types of Contact Lenses, 2019, pp. 1-2 [online], [retrieved Apr. 26, 2023], retrieved from the Internet <URL: https://www.nei.nih.gov/learn-about-eye-health/healthy-vision/contact-lenses/other-types-contact-lenses>. (Year: 2019).*
Simon Winter, Transverse Chromatic Aberration and Vision: Quantification and Impact Across the Visual Field, pp. 1-72 (2016). (Year: 2016).*
B. Swiatczak et al., Emmetropic, But Not Myopic Human Eyes Distinguish Positive Defocus from Calculated Blur, 62 Investigative Ophthalmology & Visual Science, Article 14, 1-9 (2021). (Year: 2021).*
Barbara Swiatczak et al., Myopia: Why the Retina Stops Inhibiting Eye Growth, 12 Scientific Reports 21704 (2022), 9 pages. (Year: 2022).*
Beate Spychala et al., Chromatic Dispersion of Soft Lens Materials, 46 Contact Lens and Anterior Eye 101864-1 to 101864-9 (2023). (Year: 2023).*
Jerome A Legerton et al., Myopia Regulation: Myth or Megatrend? Many Methods Purportedly Slow the Progression of Myopia. But, Do They Really Work?, 146 Review of Optometry 68+ (2009). (Year: 2009).*
Aldo Vagge et al., Prevention of Progression in Myopia: A Systematic Review, 6 Diseases 1-25 (2018). (Year: 2018).*
Katarzyna Zorena et al., Early Intervention and Nonpharmacological Therapy of Myopia in Young Adults, 2018 Journal of Ophthalmology 1-11 (2018). (Year: 2018).*
Jeffrey J. Walline et al., Effect of High Add Power, Medium Add Power, or Single-Vision Contact Lenses on Myopia Progression in Children, 324 JAMA 571-580 (2020). (Year: 2020).*
Gawne, et al. Juvenile Tree Shrews Do Not Maintain Emmetropia in Narrow-Band Blue Light. Optom Vis Sci. Oct. 2018. pp. 911-920. vol. 95, Issue 10.
Zhao, et al. Role of Short-Wavelength Filtering Lenses in Delaying Myopia Progression and Amelioration of Asthenopia in Juveniles. Int J Ophthalmol. Aug. 18, 2017. pp. 1261-1267. vol. 10 Issue 8.
Siegwart, et al. Binocular Lens Treatment in Tree Shrews: Effect of Age and Comparison of Plus Lens Wear With Recovery From Minus Lens-Induced Myopia. Experimental Eye Research. 2010. vol. 91 Issue 5. pp. 660-669.
Norton, et al. The Effect of Age on Compensation For A Negative Lens and Recovery From Lens-Induced Myopia in Tree Shrews (Tupala glis belangeri). Vision Research. Mar. 17, 2010. vol. 50 Issue 6. pp. 564-576. Elsevier.
Amedo, et al. Visual Guidance Of Recovery From Lens-Induced Myopia In Tree Shrews (Tupaia glis belangeri). Ophthalmic Physiol Opt. Mar. 2012. vol. 32, Issue 2. pp. 89-99.

(56) References Cited

OTHER PUBLICATIONS

Wikipedia. Fresnel Lens. Created Jul. 24, 2002. Last Modified Apr. 5, 2021.
Walline, JJ et al., "Multifocal Contact Lens Myopia Control" Optometry and Vision Science; Nov. 2013; 90(11); 1207-1214.
Anstice, NS, et al., "Effect of Dual-Focus Soft Contact Lens Wear on Axial Myopia Progression in Children" Ophthalmology; Jan. 26, 2011; 118(6): 1152-1161.
Turpin, S. "Assessment of Three Multifocal Soft Lens Designs for Myopia Control." (2016); available at https://www.semanticscholar.org/paper/Assessment-of-Three-Multifocal-Sof-Lens-Designs-Turpin/582b6a70af7d0c80e2541a58d4715e759c10259a.
Zhu, Q et al. Retardation of Myopia Progression by Multifocal Soft Contact Lenses:; Jan. 1, 2019; International Journal of Medical Sciences; 16(2): 198-202.
Bahng Seung Hoon, "Written Opinion of the International Searching Authority" for International Application No. PCT/US2020/048788, Dec. 10, 2020.
Read, S. A., M. J. Collins and B. P. Sander (2010). "Human optical axial length and defocus." Invest Ophthalmol Vis Sci 51(12): 6262-6269.
Chiang, S. T., J. R. Phillips and S. Backhouse (2015). "Effect of retinal image defocus on the thickness of the human choroid." Ophthalmic Physiol Opt 35(4): 405-413.
Gawne et al., "Chromatically Simulated Myopic Blur Counteracts a Myopiagenic Environment," Experimental Eye Research, vol. 222, Sep. 2022.

\* cited by examiner

CHROMATIC ABERRATION TUNING OPHTHALMIC CORRECTOR LENS METHODS

RELATED APPLICATION

This application claims priority to U.S. Provisional Patent Application No. 62/951,869, filed on Dec. 20, 2019, and entitled "Chromatic Aberration Tuning Opthalmic Corrector Lens Method," which is incorporated herein by reference.

STATEMENT REGARDING FEDERALLY SPONSORED RESEARCH OR DEVELOPMENT

This invention was made with government support under EY028578 awarded by the National Institute of Health. The government has certain rights in the invention.

TECHNICAL FIELD

The present disclosure is directed to methods of tuning chromatic aberration using hybrid lens for the treatment of myopia.

RELATED ART

There is a significant increase in the number of young people needing corrective glasses and in the powers of correction needed. In particular, many young people have myopia, or near-sightedness, where light is focused in front of the retina rather than on the retina, as would be the case for those with no visual defects. It is believed that there is some effect driven by the chromatic aberration of the eye that is driving this increase in those with visual defects. To test this theory, it has been proposed to make corrective lenses that provide different powers of correction across the lens (e.g., spatially varying the power) and then painting on, adding a dye or applying a coating to the lens, resulting in the powers being associated with specific colors. As an example, the parts of the lens that pass red light may be +1D (diopter) power and the parts of the lens that pass blue light may be −1D power. The color selection may be achieved by putting dyes on the lens at the correct locations to pass or block the red or blue light.

The present disclosure involves a different and simple way to produce and use a lens to treat myopia. The present methods utilize a "hybrid" lens with a large amount of chromatic aberration so that, instead of blocking light, one has a lens that has both better transmission and a desired state of chromatic aberration. The hybrid lens contains optical power that is refractive and diffractive, with a distribution of power varied between the refractive and diffractive portions to achieve the desired state of chromatic aberration to treat myopia of a patient.

BRIEF DESCRIPTION OF DRAWINGS

The present disclosure can be better understood, by way of example only, with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure is generally directed to methods of treating visual defects and producing lenses for treating visual defects. More specifically, the present disclosure includes treatment of myopia using a "hybrid" lens that results in a desired state of chromatic aberration for the subject using the lens. The desired state of chromatic aberration is determined for each individual by first assessing refractive error of the eyes of the individual using one individual or several individual colored lights. Changes to the focus of each colored light (i.e., blue, green, red light) to produce the desired state of chromatic aberration are determined, and a hybrid lens is designed and produced by altering diffractive and refractive portions of the lens to change the distribution of power accordingly.

Chromatic aberration means that light of different colors does not focus on the same image point. In chromatically uncorrected refractive systems, blue light generally focuses closer to the lens than green and red light. This is true for the human eye, as well, as it is a refractive optical system with rods and cones for sensing the light focused onto it. With regard to the observed increase in younger people in need of corrective vision, it is possible that eye growth that occurs during a person's youth is attempting to reach a particular balance of blue and red energy at the retina, and that this balance is disrupted for reasons that have yet to be fully understood.

It is believed that the eye grows based on the colors sensed. The fundamental chromatic aberration of the eye is such that red light focuses further into the eye than green and blue. For example, when the retina is located such that the blue is perfectly at focus, the retina would sense that the blue brightness would be larger than the red brightness because the red light is out of focus. This input may influence eye growth so that the red irradiance increases to eventually match the blue.

Figure 1:
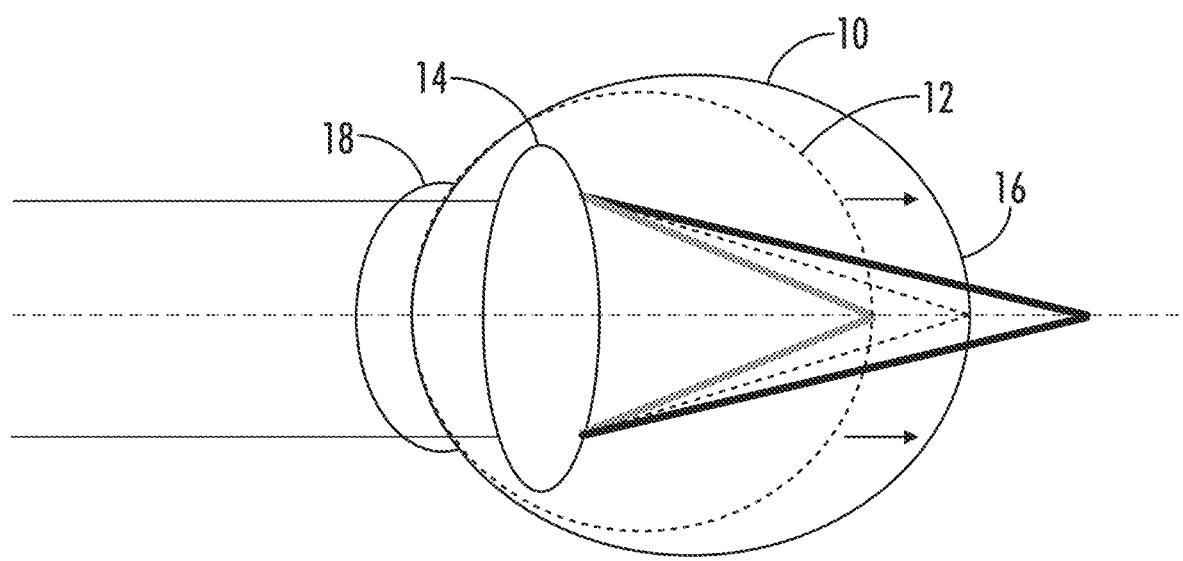
FIG. 1 is a schematic illustrating a fully grown eye with no visual defects (solid outline) and light focused on the retina. Within the outline of the grown eye is a growing eye with visual defects (dotted outline). The light is depicted as blue light (solid grey line), green light (dashed line), and red light (black solid line).

Referring to FIG. 1, there is depicted a schematic of an eye in a fully grown state and a growing state. When an individual is young, the eye grows in length and diameter, and this growth typically ends when the individual is between the ages of 20-30. The dotted outline of the eye in FIG. 1 represents the growing eye 12, while the solid outline represents the fully grown eye 10. A fully grown eye 10 may reach approximately or greater than 24 millimeters (mm). Briefly, the eye operates by having light enter through the cornea 18 and the pupil, with the opening represented by the pupil being controlled by the iris. Light then passes through the eye's lens 14, which, with the cornea 18, act to focus the light on the retina 16. Photoreceptors convert the light into electrical signals, which then travel from the optic nerve to the brain and are interpreted as images. The eye contains rods and cones that sense the focused light, and cones preferentially sense "red", "green", and "blue" light.

Figure 2:
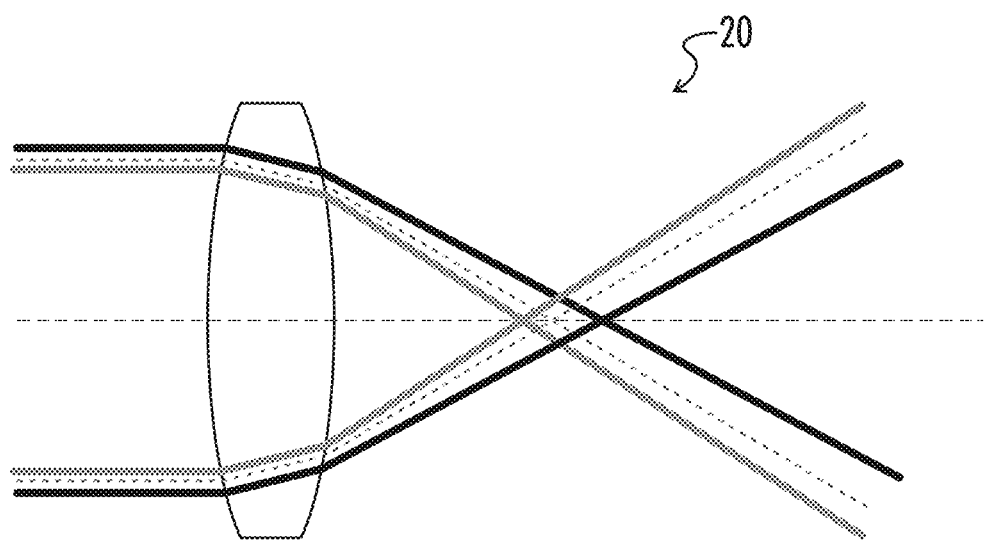
FIG. 2 is a schematic illustrating refractive lens dispersion, with blue light (solid grey line) focused closest to the lens, followed by green light (dashed line), and then red light (solid black line).
Figure 3:
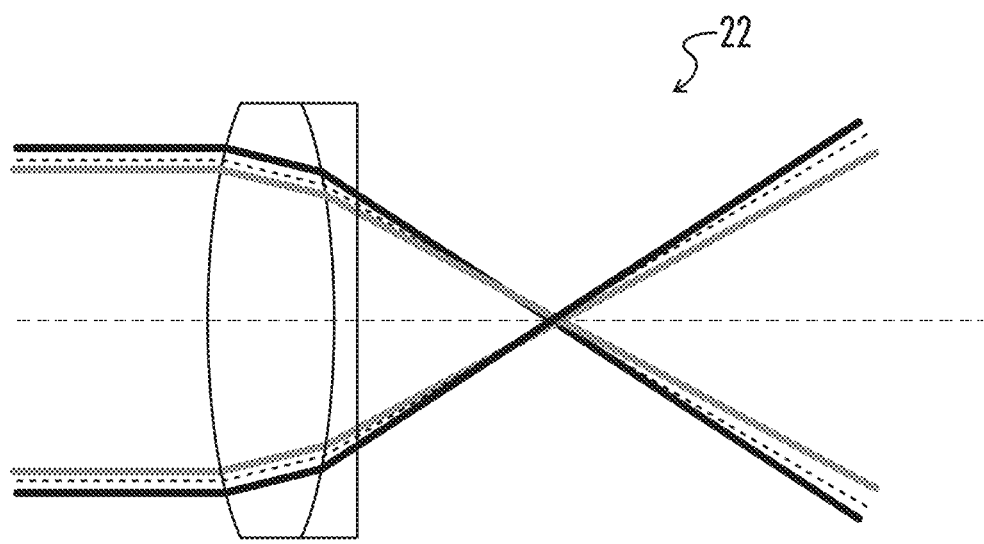
FIG. 3 is a schematic illustrating achromatic dispersion, with blue light (solid grey line), green light (dashed line), and red light (solid black line) displayed. Blue light and red light at the ends of the spectral band are focused closely together.

The eye's lens 14 and cornea 18 refract light to focus on the retina 18. Many visual defects occur based on how light is refracted. For an eye without visual defects, as shown by the fully grown eye 10 in FIG. 1, light rays form an image at the retina. However, myopia occurs when light rays form an image in front of the retina and hyperopia occurs when light rays form an image behind the retina. The eye, as a refractive system, focuses blue light closest to the lens, followed by green, and then red light, as shown by the refractive lens system 20 in FIG. 2. Corrective vision lenses change the apparent refraction of the eye to alter where an image is formed relative to the retina, and thus changes the focal point of the incoming light. However, the focal points of each color light making up the incoming light (e.g. red, blue, green light) are not corrected individually and to potentially different extents. The power of a lens is expressed in diopters (D), where a negative power lens is used to correct myopia by moving the focal point further from the lens. A diffractive lens (not depicted), flips the order of focused light, with red light focused closest to the lens, followed by green light and then blue light. A diffractive lens has the opposite sign of dispersion as a refractive lens, and it is generally 10 to 25 times more dispersive. An achromatic lens 22, as shown in FIG. 3, has one positive power and one negative power portion and is used to converge the focal points of light. The fractional amount of color spread depends on the lens material (dispersion). To make an achromatic lens 22, a positive power lens of one material is mated with, and sometimes bonded, to a negative power lens of another material so that the addition of element powers results in the desired lens power and so that the dispersion of the positive element balances the dispersion of the negative element. This balance of dispersion minimizes the longitudinal spread of light from color.

While typical corrective lenses change the focal point of light, a hybrid lens can be used to adjust the focal points of individual colored light differently. For example, the hybrid lens may include parts or structures of the lens that pass red light at one power (e.g., a +1D power) and that pass blue light at different power (e.g. a −1D power).

Figure 4:
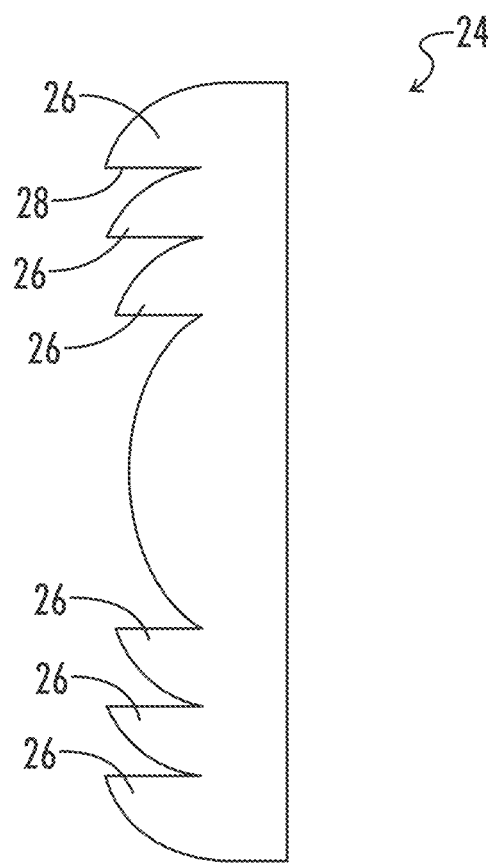
FIG. 4 is a schematic illustrating a Fresnel lens having annular steps.

Referring to FIG. 4, a Fresnel lens 24 is shown, with annular steps 26, also referred to as "facets," with each step 26 having a depth 28, as shown in FIG. 4. In some instances, depth 28 is such that the optical path of light passing through the peak of an annular step 26 differs by one wave from the optical path of light passing through the base of the annular step 26 at a selected wavelength. However, other depths are possible and compatible with the present disclosure. A selected wavelength is determined as a wavelength in approximately the middle of the spectrum band of interest. For example, for visible light, a green wavelength may be chosen as the wavelength of interest, where green light is represented by a wavelength between approximately 495 nm and 570 nm. In some instances, the selected wavelength is a green light of approximately 550 nm. A selected wavelength in approximately the middle of the spectrum band is chosen because the lens is most efficient at that wavelength, with the efficiency decreasing further from that wavelength in a symmetrical manner. In the instance where a green wavelength is selected, red and blue wavelengths further from the green wavelength will be less efficient. Efficiency is described in regard to the amount of light that goes through the lens to a desired focal point. In some instances, the selected wavelength has approximately 100% efficiency, while lower efficiencies further from the selected wavelength range from approximately 85-90% efficiency.

The steps 26 can act as diffractive structures for a lens. The diffractive lens pattern appears similar to a bull's eye with the zones thinning as they approach the lens edge, and each zone contributing one wave of path length change. All wavelengths see the same lens structure, but because one wave of red light is longer than one wave of blue light, the effect of the lens steps 26 on red light is stronger in proportion to the ratio of the wavelengths. Hybrid lenses may include structures, such as the diffractive structures of a Fresnel lens 24, to adjust individual focal points of red, blue, and/or green light each by a desired amount, each.

In some embodiments, the refractive and diffractive features of a hybrid lens are independently controlled to provide independent tuning of certain wavelength ranges, such as red, green, or blue, to achieve a desired state of chromatic aberration for training eye growth in a manner to treat myopia. As an example, the power for a first wavelength range (e.g., blue light or other color component) may be controlled so that that the focal point for the wavelength range is shifted by a first amount to or from the retina, and the power for an second wavelength range (e.g., red light or other color component) may be independently controlled from the tuning of the first wavelength range so that the focal point for the second wavelength range is shifted by a second amount to or from the retina. Both wavelength ranges may be shifted by the same or different extents in the same direction relative to the retina, or the wavelength ranges may be shifted in opposite directions. As an example, to train the eye to grow in a manner for reducing the effect of blue light on eye growth, the focal point of blue light may be shifted away from the retina without a corresponding shift to the focal point of red light. In this regard, the total power of the lens to red light may be controlled such that there is no substantial shift of the focal point for red light or the focal point for the red light is shifted in some manner different than the focal point for the blue light. In some embodiments, as will be described in more detail below, the focal points of different wavelength ranges of light are independently shifted so that eye growth is controlled in a desired manner, such as eliminating or reducing myopia.

Figure 5:
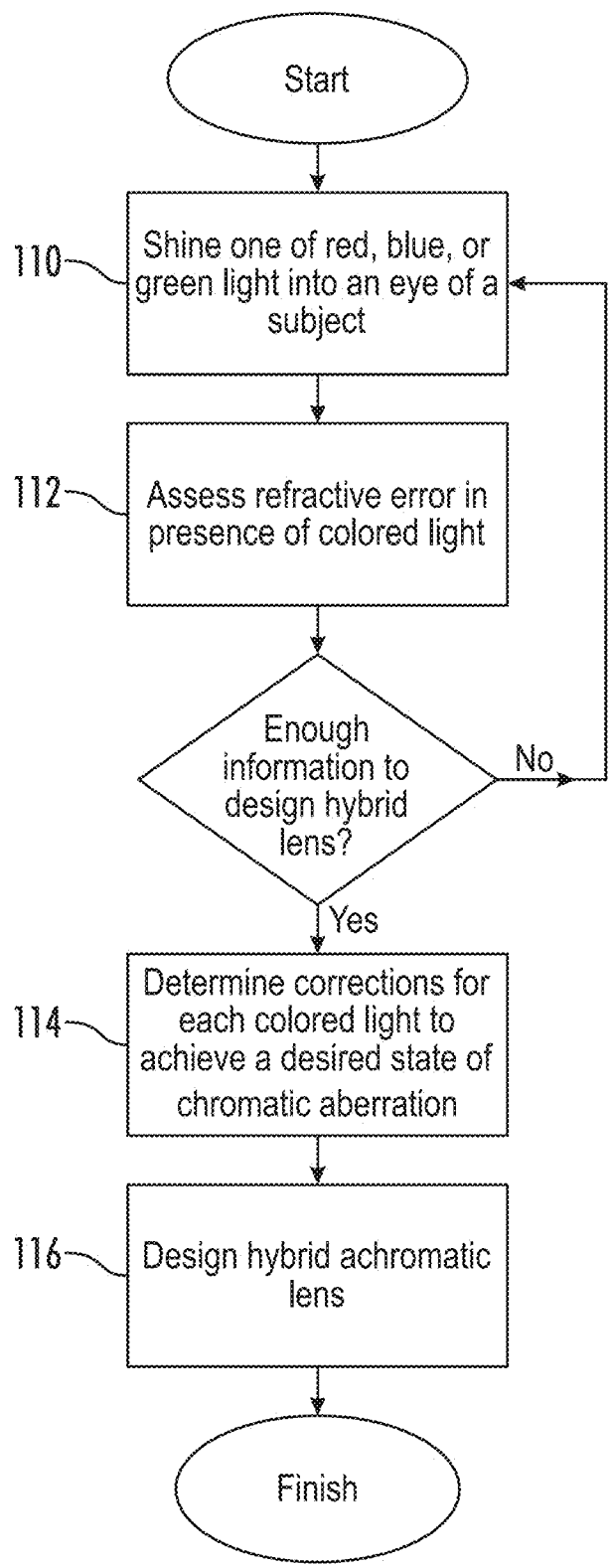
FIG. 5 is a flowchart illustrating an exemplary method of providing a hybrid lens for use in training eye growth to treat myopia in a subject.

In FIG. 5, there is depicted a flowchart describing a method of providing a hybrid lens for use in training eye growth to treat myopia in a subject. The method involves a first step of assessing the vision of the subject. In some instances, the subject is an individual who has myopia or is suspected of having myopia. The subject may have previously had a vision test to assess refractive errors or may have had no previous examination. In some instances, the eyes of the subject have not completed their growth and are still growing in length and diameter. In some instances, the eyes of the subject are fully grown and have reached their maximum size.

In step 110 of FIG. 5, the subject's eyes are tested under the conditions of exposure to a color component of visual spectrum light. The color component is composed of a subset of the wavelengths that make up the visual spectrum light. In some instances, this color component is red, blue, or green light, but other color components of different wavelength ranges are possible. Red light may have a wavelength between about 620 nanometers (nm) to 750 nm. Blue light may have a wavelength between about 450 nm and 495 nm. Green light may have a wavelength between about 495 nm and 570 nm. The color component light is shined into the eye or eyes of the subject, who is then tested to assess refractive error under the conditioned of the colored light.

Assessment is undertaken using methods known in the art, but using one color component of visual spectrum light instead of light consisting of the entire visible light spectrum, as shown in step 112 of FIG. 5. In some instances, assessment is done by using a phoropter, with the subject describing when an image is most clear as different lenses are used under the color component light condition. In some instances, visual acuity is assessed using an eye chart under the single color component light condition, with the subject reading or describing an image or images. In some instances, the testing is manually administered by an ophthalmologist or other vision professional, who observes and determines the refractive error under each color component light condition. In other instances, the testing is undertaken using an automated method or device that administers and determines refractive error, such as those used in assessment for laser-assisted in situ keratomileusis (LASIK) surgery.

One color component is used to determine all corrective parameters needed to design the hybrid lens in some cases, while in other cases testing is done using two or more of red, green, or blue light individually, to determine the corrective parameters and refractive error necessary for lens design. This testing using more than one color component, individually, is shown by the repeat step in FIG. 5. In some instances, other parameters contribute to the design of a hybrid lens, where the parameters include, but are not limited to, the patient's age, eye size, or other parameters described by statistical models from data of similar patients. Assessment of the eye is conducted once for the fitting of the hybrid lens in some instances, while in other instances more than one assessment is undertaken to determine the change in refractive error for the patient. In cases where multiple assessments are undertaken, a new hybrid lens for the patient may be designed.

In step 114 of FIG. 5, corrections are determined based on the results of the assessment using each colored light. These corrections involve the adjustment of the focal point for each of red, blue, and green light, or a subset thereof. The changing in these focal points is undertaken to create a desired state of chromatic aberration, such that visual defects, such as myopia, are reduced or eliminated by the resulting hybrid lens.

Chromatic aberration is adjusted by varying the power distribution between refractive and diffractive portions of the hybrid lens, as shown in FIG. 5, step 116. This allows the hybrid lens to be designed having a desired amount of chromatic aberration in a thin lens.

A hybrid achromat may include a refractive lens and a diffractive lens. Since the dispersion of a diffractive lens is opposite to that of a refractive one, this hybrid achromat may be made by putting together a + power refractive lens and a + power diffractive lens. Depending on the desired chromatic state, the power distribution could be +/−, −/+ or −/− with respect to the refractive and diffractive lens power. The element powers may add up to the power of the desired lens.

In some embodiments, a computer system (not specifically shown) may be used to assist in the design of a hybrid lens 30. In this regard, the computer system may have an input interface, such as a keyboard or mouse, for receiving user inputs. The results of assessing a patient's eye in the presence of one or more color components may be input to the computer system via the input interface. As an example, for each tested color component, a value indicative of the refractive error assessed for the respective color component may be input by a user. Based on these values, the computer system may calculate or otherwise determine a desired focal point shift for one or more color components and then design a hybrid lens having the desired focal point shifts. As an example, the curvature of the hybrid lens may be selected or otherwise determined to achieve a desired refractive dispersion, and the shapes and sizes of the facets may be determined to achieve a desired diffractive dispersion such that the focal points are shifted in a desired manner. Information indicative of the design, such as the dimensions of the hybrid lens, may be displayed or otherwise output by an output interface of the computer system, such as a display device or a printer.

Notably, the computer system may be implemented in hardware or any combination of hardware and software. As an example, the computer system may have one or more processors for executing software or firmware to achieve the ascribed functions of the computer system. In other embodiments, other techniques for designing a hybrid lens are possible.

Figure 6:
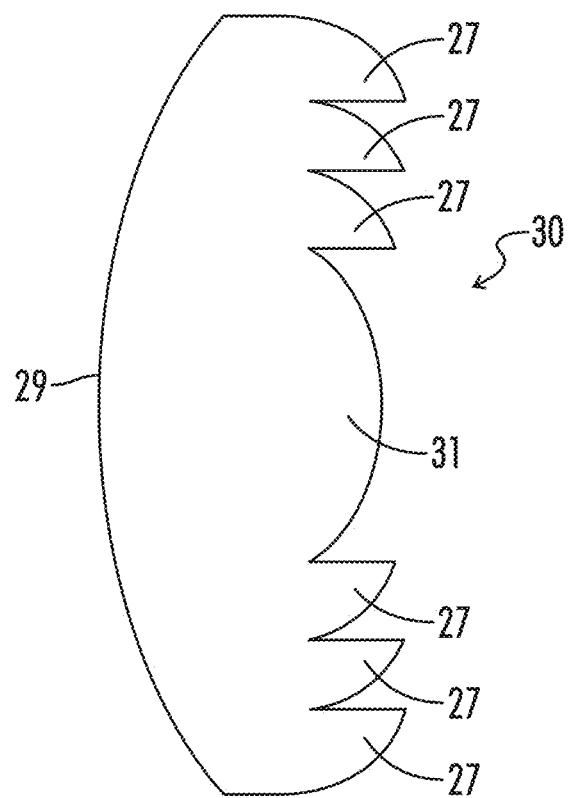
FIG. 6 is a schematic illustrating a first embodiment of a hybrid achromatic lens provided by a method of the present disclosure to treat myopia, with diffractive structures on a planar face and a refractive portion.

Referring now to FIG. 6, one embodiment of a hybrid lens 30 is displayed. In this embodiment, hybrid lens 30 has a curved, convex surface 29 that is a refractive portion and a planar face 31 located approximately opposite the curved surface 29. The planar surface 31 has a diffractive portion, which is a plurality of diffractive facets or steps 27 similar to those of a Fresnel lens. Thus, the curvature of surface 29 is a refractive feature that affects power, and the facets 27 are diffractive features that also affect power. Diffractive facets 27 have different dimensions and sizes in different embodiments not shown. However, in the depicted embodiment, the step height of diffractive facets 27 on hybrid lens 30 are such that they create an optical path length one wavelength for a wavelength near the center of the visible spectrum.

Figure 7:
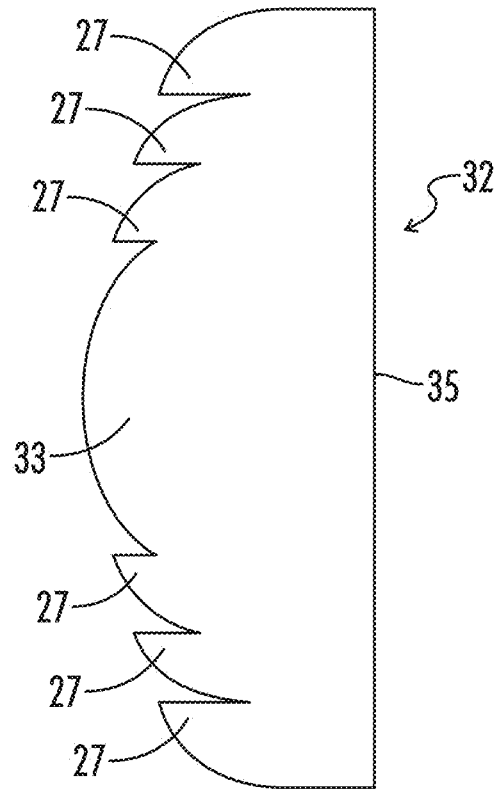
FIG. 7 is a schematic illustrating a second embodiment of a hybrid achromatic lens provided by a method of the present disclosure to treat myopia, with diffractive structures on a curved, refractively powered face and an opposite, planar face.
Figure 8:
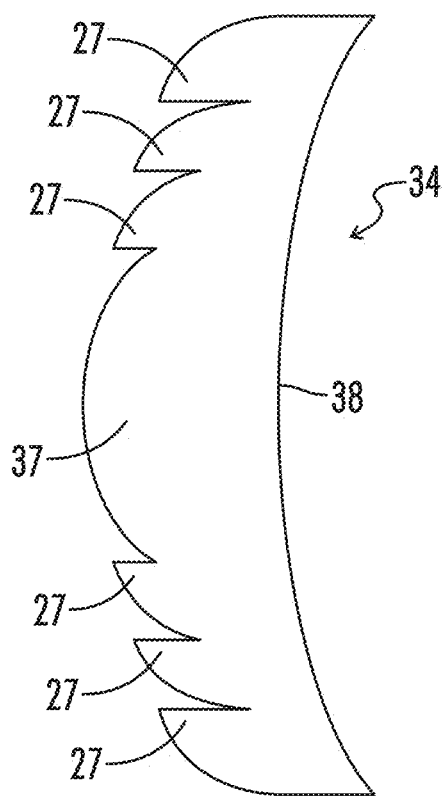
FIG. 8 is a schematic illustrating a third embodiment of a hybrid achromatic lens provided by a method of the present disclosure to treat myopia, with diffractive structures on a curved, refractively-powered face and an opposite, concave portion.
Figure 9:
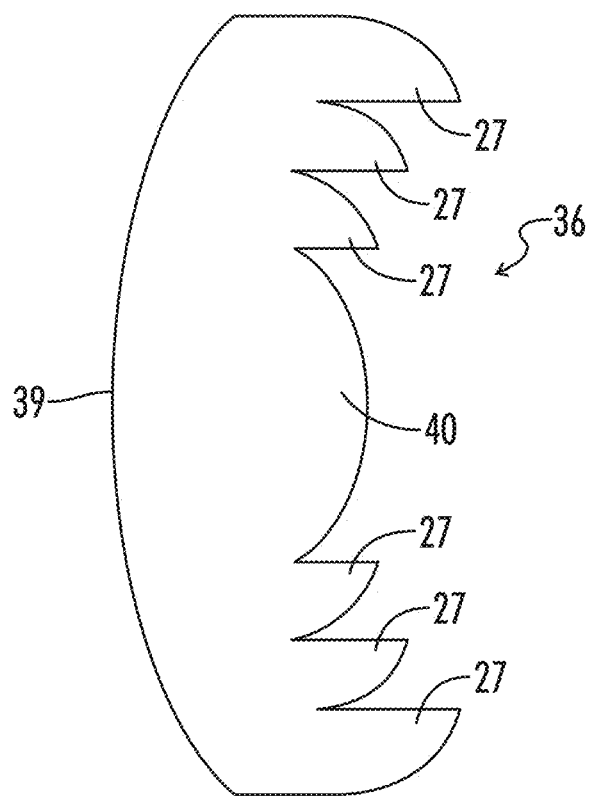
FIG. 9 is a schematic illustrating a fourth embodiment of a hybrid achromatic lens provided by a method of the present disclosure to treat myopia, with diffractive structures on a curved face and an opposite, refractively-powered portion.

In other embodiments, diffractive facets 27 are present on a curved surface that is refractive in nature. For instance, in FIG. 7, diffractive facets 27 are on a curved, refractively-powered side 33 that is opposite a planar side 35 of hybrid lens 32. In FIG. 8, diffractive facets 27 are also on a curved, refractively-powered side 37, but in this embodiment, the diffractive facets 27 are opposite a concave face 38 of hybrid lens 34. In FIG. 9, diffractive facets 27 are on a curved, concave side 40 opposite a convex, refractively-powered face 39 of hybrid lens 36. Thus, in the methods of the present disclosure, lenses designed to treat myopia by achieving a desired state of chromatic aberration can have diffractive facets 27 or other types of diffractive structures on the same surface as the refractively-powered portion of the hybrid lens or on a surface separate from the refractively-powered portion. Hybrid lenses may have one or both surfaces that are curved, with either or both sides containing diffractive facets 27 or other types of diffractive structures. In some embodiments, one side of hybrid lens is concave, while the other side is convex, resulting in a hybrid lens shaped in a "meniscus"-like manner. The shape of lenses compatible with the present methods are in some, but not all, instances spherical. For instance, they may be aspherical, free form, contain annular zones of different powers, or include arrays of lenslets of similar or different powers. Diffractive phase functions of hybrid lenses compatible with the present disclosure may or may not be rotationally symmetric, and can take any functional form in order to achieve some desired field dependent chromatic aberration and/or power distribution.

Initially, hybrid lenses consistent with use with the disclosed methods may be produced for use and testing on tree shrews. Manufacturing of lenses compatible with the present disclosure is in some instances undertaken using diamond turning of plastic and in other instances undertaken using injection molding. Injection molding manufacture is compatible with mass manufacturing, though other manufacturing methods of lenses are compatible with the present disclosure. Lenses are in some instances spectacle lenses for eye glasses. In these instances, lenses are manufactured from plastic, which is, for example, polycarbonate, trivex, "CR 39" plastic, or high-index plastic. However, other materials, such as glass, or other plastics are compatible with the present disclosure. Lenses in other instances are contact lenses, which are composed of hydrogel materials, such as silicone hydrogel. In some instances, contacts are rigid gas permeable lenses composed of acrylate, silicone, and fluorine. In some instances, contacts are hybrid contacts composed of acrylate-silicone-fluorine in the center of the lens and silicone hydrogel near the edges of the lens. However, other contact lens materials are compatible with the present disclosure.

Figure 10:
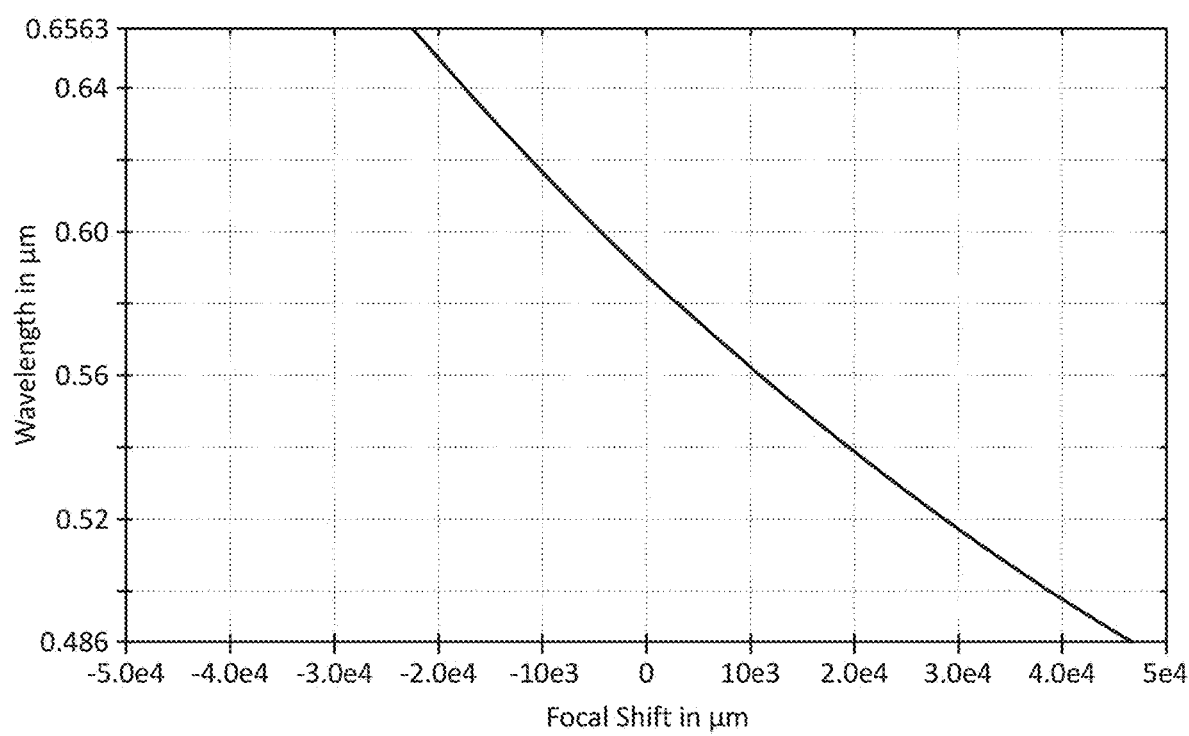
FIG. 10 is a graphical representation of focus position versus wavelength for a hybrid lens with diffractive structures on a planar side of the lens and a refractively-powered opposite portion, such as the lens of FIG. 6. There is a maximum focal shift range of approximately 69,375 µm and a diffraction limited range of approximately 150 µm.
Figure 11:
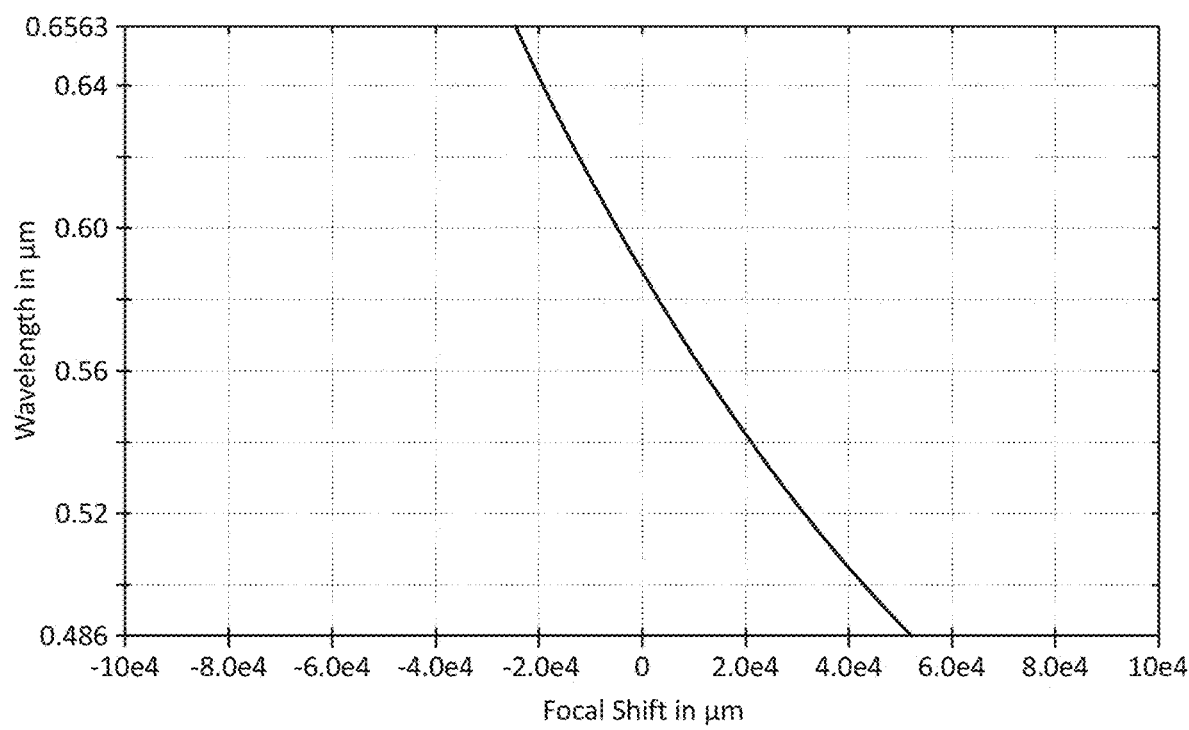
FIG. 11 is a graphical representation of focus position versus wavelength for a hybrid lens with diffractive structures on a planar side of the lens and a refractively-powered opposite portion, such as the lens of FIG. 6. There is a maximum focal shift range of approximately 76,235 µm and a diffraction limited range of approximately 150 µm.
Figure 12:
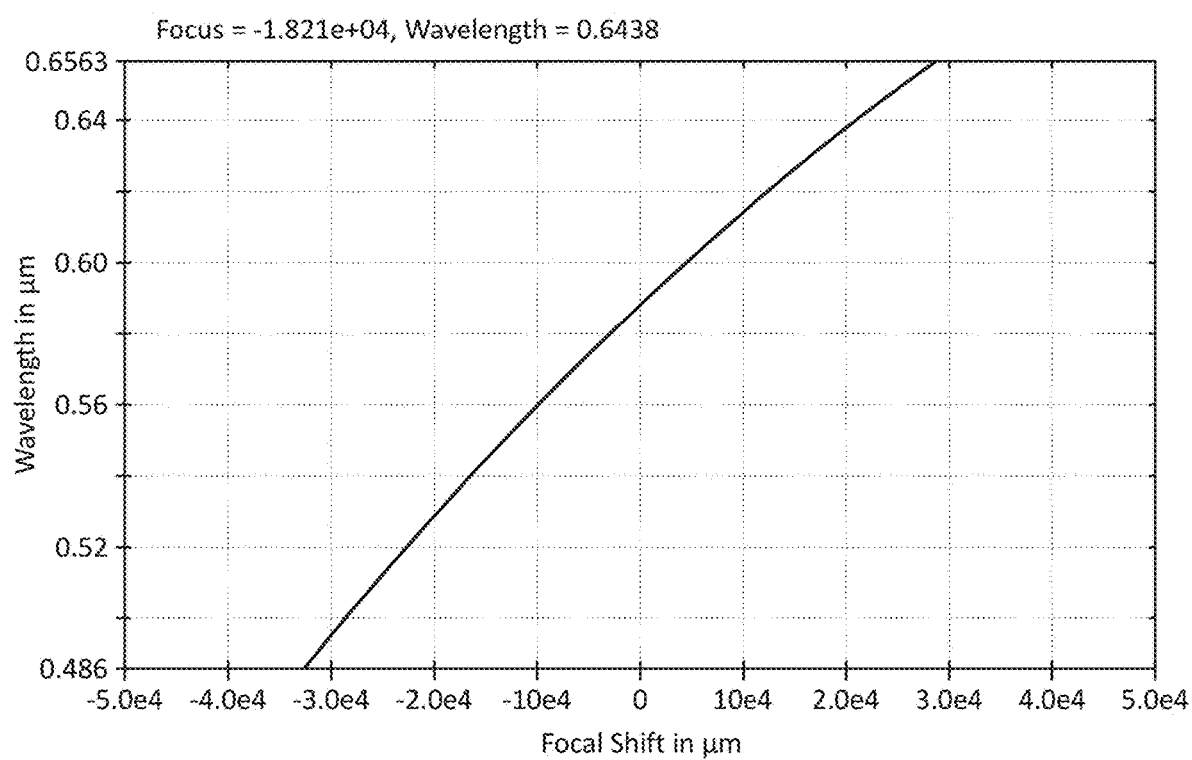
FIG. 12 is a graphical representation of focus position versus wavelength for a hybrid lens with diffractive structures on a planar side of the lens and a refractively-powered opposite portion, such as the lens of FIG. 6. There is a maximum focal shift range of approximately 61,271 µm and a diffraction limited range of approximately 155 µm.
Figure 13:
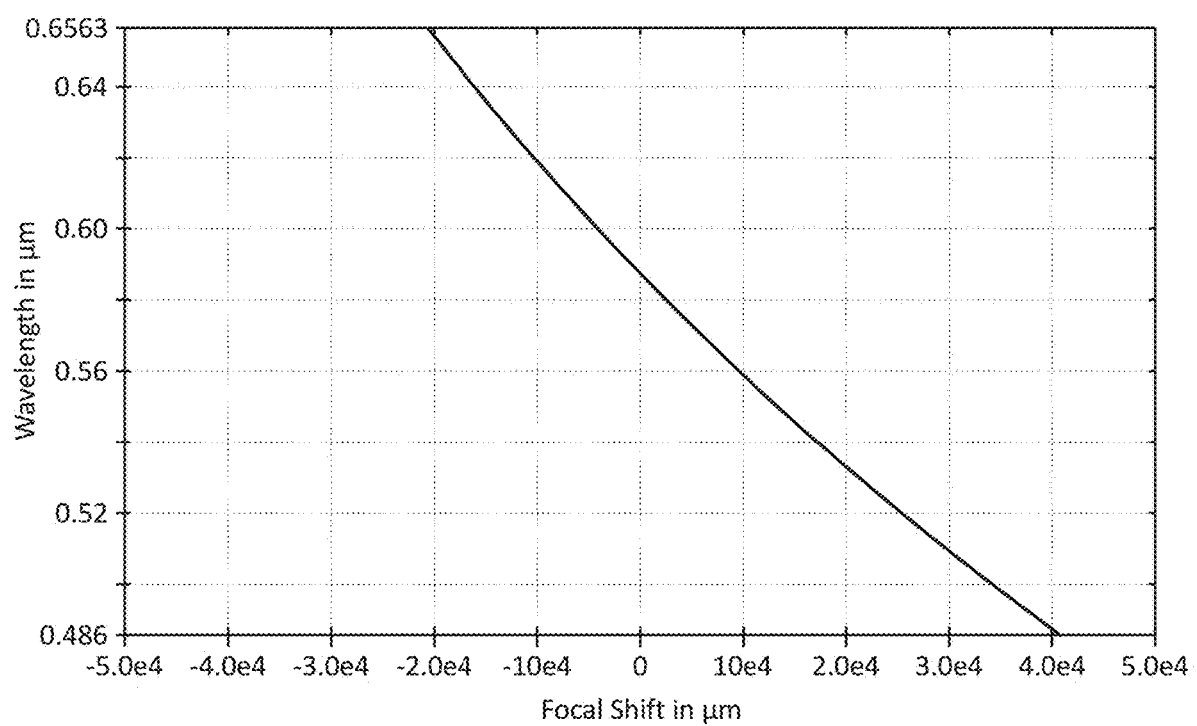
FIG. 13 is a graphical representation of focus position versus wavelength for a hybrid lens with diffractive structures on a curved side of the lens and a refractively-powered opposite portion, such as the lens of FIG. 9. There is a maximum focal shift range of approximately 61,406 µm and a diffraction limited range of approximately 150 µm.

Referring to FIG. 10 through FIG. 13, hybrid lenses with different relative powers of refractive and diffractive elements are used to tune chromatic aberration, with plots representing the variation of focal position versus wavelength. The plots in FIG. 10 through FIG. 13 highlight that tuning of chromatic aberration can be undertaken in terms of both magnitude and sign of error. FIG. 10 shows a plot for a hybrid lens 30 similar to that of FIG. 6, with diffractive structures on a planar surface and a curved refractive surface opposite the planar surface of hybrid lens 30. The lenses that were used to produce the plots in FIG. 11 and FIG. 12 were similar to that of FIG. 10, but have different relative powers of diffractive and refractive elements. Thus, the maximal focal shift ranges for the different lenses varies, with a range of approximately 69,375 micrometers (μm) for FIG. 10, approximately 76,235 μm for FIG. 11, and approximately 61,271 μm for FIG. 12. Notably, the lens used in FIG. 12 also changes the direction of chromatic aberration relative to the direction shown in the graphs of FIG. 10, FIG. 11, and FIG. 13. In FIG. 13, there is displayed a plot produced by a hybrid lens similar to the hybrid lens 36 of FIG. 9. The maximal focal shift for FIG. 13 is approximately 61,406 μm.

Figure 14A:
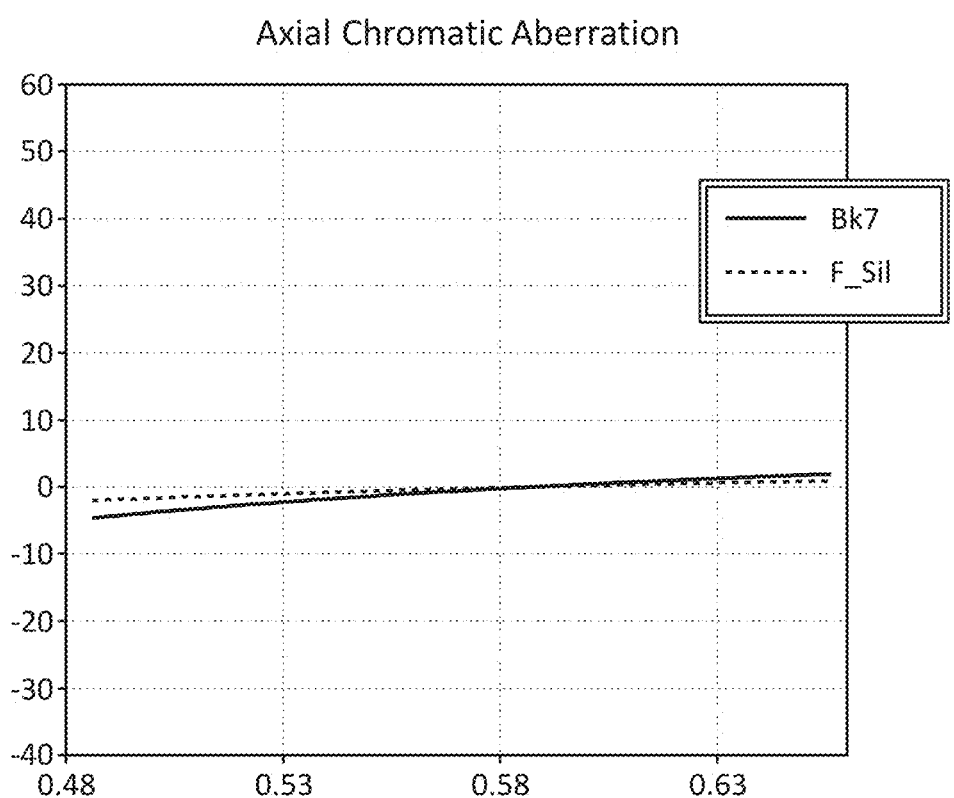
FIG. 14A is a graphical representation of focus position versus wavelength for several lens.
Figure 14B:
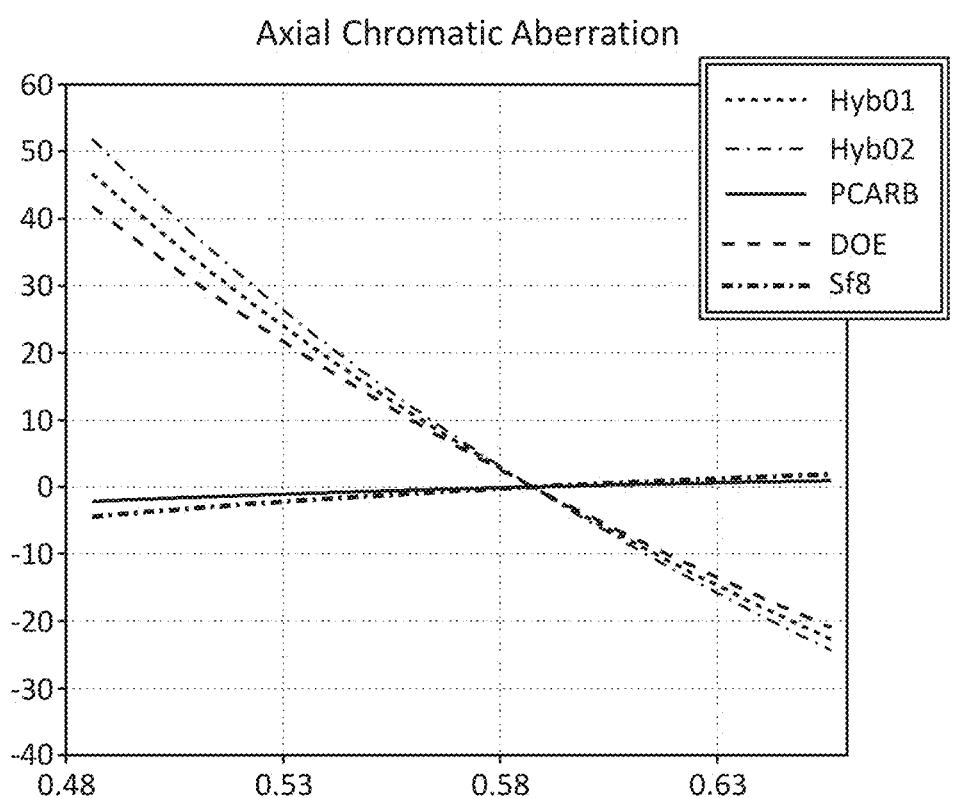
FIG. 14B is a graphical representation of focus position versus wavelength for several lens, including the lens producing the graphs of FIG. 10 and FIG. 11.
Figure 14C:
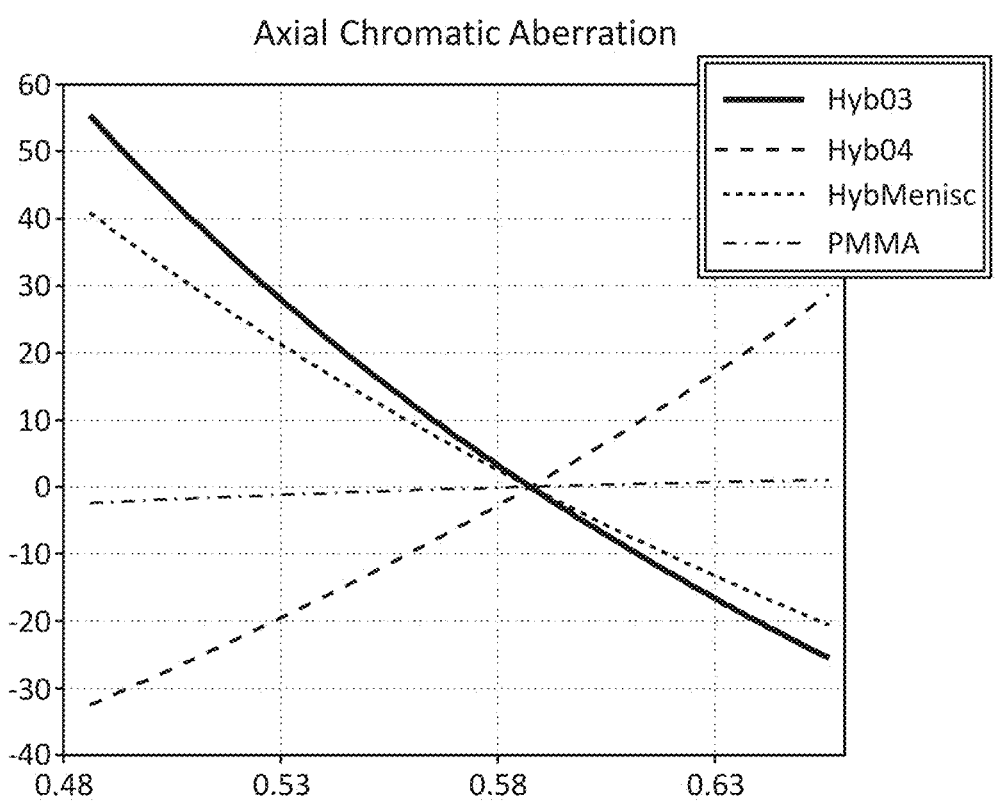
FIG. 14C is a graphical representation of focus position versus wavelength for several lens, including the lens producing the graphs of FIG. 12 and FIG. 13.

In FIG. 14A through FIG. 14C, plots display the chromatic focal shifts for a plurality of lenses, showing how the ranges can be adjusted in order to achieve the methods of the present disclosure. However, the ranges displayed in FIG. 14A through FIG. 14C do not explore the full range possible for lenses and hybrid lenses.

For the disclosed methods, once myopia is diagnosed, lenses are developed and used to treat myopia and potentially to stop or slow its advancement. As there is a correlation between extreme myopia and certain eye diseases, such as cataracts and retinal disorders, the disclosed methods also function as a means of preventing or reducing the occurrences of these disorders.

Over the last few years there has been a significant increase in the number of people developing myopia and adverse effects of myopia have generally become more pronounced. It is believed that environmental factors, such as screen use, affect how the eye grows relative to blue light in particular. When the eye senses blue brightness to be larger than the red brightness, the input can influence eye growth so that the red irradiance increases to eventually match the blue. It is further believed that increased usage of electronic devices, such as smartphones, computers, televisions, etc. by children has led to a greater exposure of blue light that adversely affects eye growth in a way that leads to myopia and other visual defects later in life. In some embodiments, the present methods are used to train the eye to mitigate the effects of blue light exposure on eye growth. In these instances, a hybrid lens may be designed to have a stronger + power for blue wavelengths. As such, the hybrid lens is configured to amplify chromatic aberration so that blue light focuses closer to the eye's lens and cornea than it would without the hybrid lens. Notably, this shifting of blue light may occur without a corresponding shift in other color components, such as red light. That is the refractive (e.g., curvature) and diffractive (e.g., facets) features may be independently controlled so that the overall effect is to increase the power of the hybrid lens for one wavelength range (e.g., blue light), thereby shifting the focal point of the blue light away from the retina, and to control the power of the hybrid lens for another wavelength range (e.g., red light) in a different manner. As an example, the power of the hybrid lens for red light may be increased by a different amount, decreased, or neither increased nor decreased.

This shifting of blue light focus away from the retina by the methods of the present invention serves to train the eye to grow in a manner that reduces or eliminates myopia. In some cases, the methods of the present invention train the eye to slow growth or not to grow at the same rate that it typically would without the use of the hybrid lens. This reduction in growth may result in the eye being less influenced by the blue light exposure from screens or other environmental causes and result in reduced myopia severity or elimination of myopia. However, in other embodiments, the hybrid lenses described herein may be configured to shift components of light in other manners as may be desired.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

We claim:

1. A method of providing a hybrid lens for use in training eye growth to treat myopia in a subject, comprising:
   a) assessing a refractive error of an eye of the subject in the presence of a first color component of a visible spectrum;
   b) designing the hybrid lens such that the hybrid lens has a refractive portion and a diffractive portion based on the refractive error, the hybrid lens having a distribution of power varied between the refractive portion and diffractive portion such that the hybrid lens produces a state of increased chromatic aberration for an eye of the subject for reducing or eliminating myopia advancement for the eye of the subject, wherein the hybrid lens is designed to shift, based on the distribution of power, a focal point of the first color component away from a retina of the eye and away from a focal point of a second color component of the visible spectrum when the hybrid lens is worn on the eye; and
   c) providing the subject with the hybrid lens.

2. The method of claim 1, further comprising assessing a refractive error of the eye in the presence of the second color component of the visible spectrum, wherein the designing is based on the refractive error of the eye in the presence of the second color component.

3. The method of claim 1, wherein the first color component has a wavelength range selected from 620 nanometers (nm) to 750 nm, 495 nm to 570 nm, or 450 nm to 495 nm.

4. The method of claim 1, wherein the first color component has a wavelength range selected from 620 nanometers (nm) to 750 nm.

5. A method providing a hybrid lens for use in training eye growth to treat myopia in a subject, comprising:
   shining a first color component of a visible spectrum into the eye of the subject;
   assessing a refractive error of the eye in the presence of the first color component;
   determining corrections for red light, blue light, and green light for achieving a desired state of increased chromatic aberration for the eye of the subject based on the refractive error, such that myopia advancement in the eye of the subject is reduced or eliminated;
   designing a hybrid lens having a diffractive portion and a refractive portion that provide the desired state of increased chromatic aberration, wherein the hybrid lens is designed to shift a focal point of the blue light away from a retina of the eye and away from a focal point of red light when the hybrid lens is worn on the eye; and
   providing the subject with the hybrid lens.

6. The method of claim 5, further comprising assessing a refractive error of the eye in the presence of a second color component of the visible spectrum, wherein the determining is based on the refractive error of the eye in the presence of the second color component.

7. The method of claim 5, wherein the first color component has a wavelength range selected from 620 nanometers (nm) to 750 nm, 495 nm to 570 nm, or 450 nm to 495 nm.

8. A method of manufacturing a hybrid lens for use in training eye growth to treat myopia, comprising:
   determining first information indicative of a refractive error of an eye of a subject in the presence of a first color component of a visible spectrum;
   determining second information indicative of a refractive error of the eye in the presence of a second color component of the visible spectrum; and
   manufacturing the hybrid lens having a refractive portion and a diffractive portion, the manufacturing comprising configuring the refractive portion and the diffractive portion based on the first information and the second information such that the hybrid lens produces a state of increased chromatic aberration for reducing or eliminating myopia advancement for the eye of the subject, wherein the hybrid lens is configured to shift a focal point of the first color component away from a retina of the eye and away from a focal point of the second color component when the hybrid lens is worn on the eye.

9. The method of claim 8, wherein the first color component has a wavelength range selected from 620 nanometers (nm) to 750 nm, 495 nm to 570 nm, or 450 nm to 495 nm.

10. The method of claim 8, wherein the first color component has a wavelength range selected from 620 nanometers (nm) to 750 nm.

* * * * *